United States Patent
McMahon

[11] 3,968,476
[45] July 6, 1976

[54] SPURIOUS SIGNAL REMOVAL IN OPTICAL PROCESSOR FINGERPRINT IDENTIFICATION APPARATUS

[75] Inventor: Donald H. McMahon, Carlisle, Mass.

[73] Assignee: Sperry Rand Corporation, New York, N.Y.

[22] Filed: July 17, 1974

[21] Appl. No.: 489,212

[52] U.S. Cl. ............ 340/146.3 E; 340/146.3 F; 250/233
[51] Int. Cl.² ........................................ G06K 9/13
[58] Field of Search ............ 340/146.3 E, 146.3 F, 340/146.3 P; 356/71; 250/567, 233, 237 G

[56] References Cited
UNITED STATES PATENTS

| | | | |
|---|---|---|---|
| 3,497,704 | 2/1970 | Holmes et al. | 340/146.3 F |
| 3,522,437 | 8/1970 | Bargh | 340/146.3 F |
| 3,771,124 | 11/1973 | McMahon | 340/146.3 E |
| 3,778,620 | 12/1973 | Lindemann et al. | 250/233 |

*Primary Examiner*—Joseph M. Thesz
*Attorney, Agent, or Firm*—Howard P. Terry

[57] ABSTRACT

An improved incoherent optical processor fingerprint identification apparatus employs a rotatable grating for inspecting the ridge orientations in a plurality of preselected finite sample areas of a fingerprint. A detector array including a plurality of detectors each related to a discrete sampled area is disposed to receive an image of the fingerprint filtered by the rotating grating. An incoherent light source and a lens and retroreflective prism assembly function in cooperation with the grating to produce an image thereof superposed on the grating itself such that minimum light is propagated to the detector array in the absence of an input fingerprint pattern whereas, in the presence of a fingerprint pattern, light is diffracted thereby to be filtered by the grating for supply to the detectors. Maximum light may occur at each detector under a condition of spatial alignment of the grating lines with the ridge lines of the related sampled area whereby the time interval between a reference orientation of the grating and the instant of maximum light at each detector may be converted to equivalent electrical signals uniquely representative of a particular fingerprint pattern. The signal to noise factor of the optical system is significantly improved by the use of a novel grating element having plural reflecting and transmitting stripes, with optically absorbing stripes interposed between them.

5 Claims, 8 Drawing Figures

SPURIOUS SIGNAL REMOVAL IN OPTICAL PROCESSOR FINGERPRINT IDENTIFICATION APPARATUS

BACKGROUND OF THE INVENTION

1. Field of the Invention

This invention relates generally to optical signal processors and more particularly to an incoherent optical signal processing line pattern or fingerprint ridge identification apparatus.

2. Description of the Prior Art

In the search for economical and fully practical ways of making automatic the identification of fingerprint and other patterns, incoherent optical processor systems have often been selected for study on the ground that expensive coherent light sources are avoided by them. In one such prior art incoherent pattern recognition device, there is employed a rotating grating for inspecting the line orientation in a plurality of preselected finite sample areas of the fingerprint pattern. A photodetector array including detectors each related to a discrete sampled area is disposed to receive an image of the fingerprint pattern filtered by the grating. An incoherent light source and a retro-reflective prism assembly cooperate with the grating to produce an image thereof superposed on the grating such that minimum light is propagated to the detector array in the absence of an input fingerprint pattern. On the other hand, in the presence of a fingerprint pattern, light is diffracted thereby to be filtered by the grating for supply to the detectors. Maximum light may occur at each detector under a condition of spatial alignment of the grating lines with the ridge lines of the related sampled area whereby the time interval between a reference orientation of the grating and the instant of maximum light at each detector may be converted to equivalent electrical signals uniquely representative of a particular fingerprint pattern.

Such an optical processor requires the use of certain optical components that are expensive, such as an aberration corrected lens, and is not fully suited to use in what will be described herein as a preferred off-axis configuration. If inexpensive or relatively short focus lenses are employed, whether or not in the off-axis embodiment, undesired light signals of considerable amplitude are generated that fluctuate in synchronism with the rotation of the grating. Since cyclic light impulses are thereby produced having substantially the same character as the desired impulse signals, relatively expensive optical components have been used out of necessity.

SUMMARY OF THE INVENTION

According to the present invention, the capability of a prior art noncoherent pattern recognition apparatus is extended and the aforementioned difficulties are overcome through the substitution of a novel rotatable optical grating element having plural reflecting and transmitting stripes, with optically absorbing stripes located between each reflecting and transmitting stripe. Spurious signals formerly present where relatively inexpensive optical elements were employed are removed. Also, the novel rotatable optical grating advantageously permits use of an optical processor configuration in which certain elements are tilted with respect to the principal optical axis of the system, as in off-axis systems.

DESCRIPTION OF THE PREFERRED EMBODIMENTS

Figure 1:
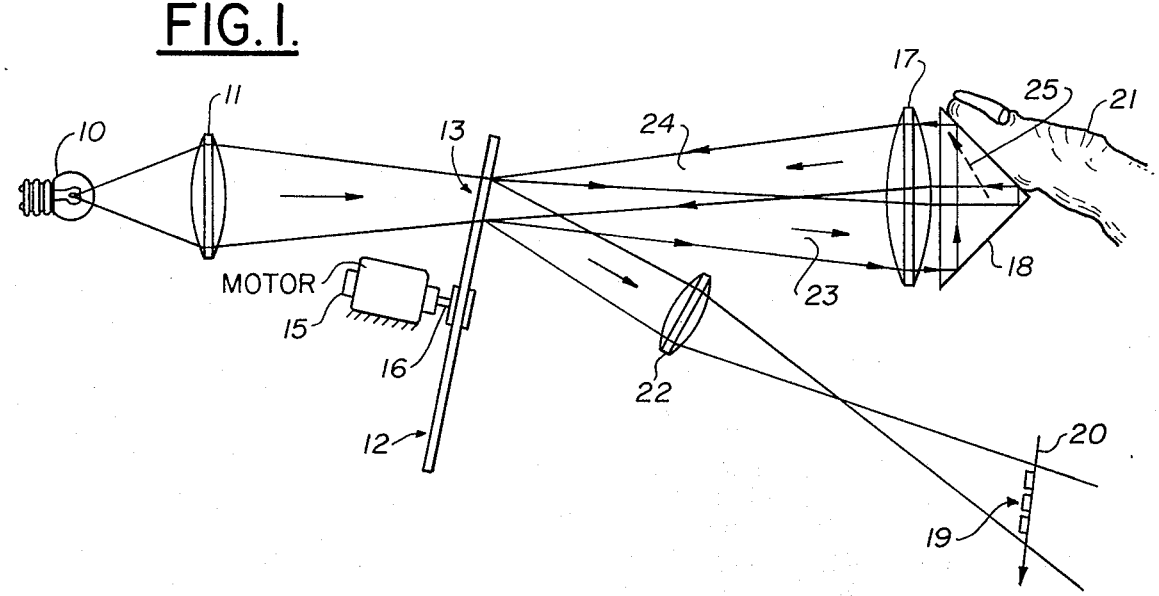
FIG. 1 is an elevation view illustrating one form of the apparatus in which the invention is practiced.

FIGS. 1, 2, 3 and 4 represent off-axis forms of the novel pattern recognition apparatus within which the present invention may be employed, but it will be understood that the invention may also be employed equally successfully in other off-axis pattern recognition devices and also in on-axis systems, including those of both types described, for example, in the McMahon U.S. Pat. No. 3,771,129 for an "Optical Processor Fingerprint Identification Apparatus", issued Nov. 6, 1973 to Sperry Rand Corporation. It will therefore be seen that the novel rotating grating system may take forms having one circular boundary or two concentric circular boundaries, for example. Though only for purposes of illustrating a preferred arrangement in which the invention may be employed, FIG. 1 is intended to show a system similar to the incoherent-light pattern recognition apparatus of FIG. 2 of the aforementioned McMahon patent.

While the invention may be employed for the recognition of a variety of different symbols or patterns made up of areas with or groups of generally parallel lines or ridges, the invention is of particular interest in the recognition of fingerprint patterns. As is generally understood, a fingerprint is normally characterized by a pattern of ridge lines having relatively constant spacing and orientation over finite small areas thereof. The present invention is based upon the inspection of the ridge line orientations in a plurality of such sampled small areas distributed generally over the area of a fingerprint. In a given fingerprint, the various ridge line orientations at the plurality of sampled positions are uniquely different from the ridge line orientations at a plurality of similar positions of any other fingerprint, provided a sufficient number of sampled areas is taken. More specifically, the present invention is based on the concepts disclosed in the aforementioned McMahon patent of utilizing a detector array having a plurality of detectors for sampling light that is diffracted from the ridge lines of a corresponding plurality of discrete finite sampled areas of the fingerprint. The detector array is used in combination with a rotating optical grating element which is imaged on itself so that no information-bearing light reaches any of the detectors in the absence of a fingerprint at the data input of the identification apparatus. When an actual finger or transparency of a fingerprint pattern is present at the data input, light is diffracted by the ridge lines. Under the condition in which the grating lines are parallel to the ridge lines of any one sampled area, a maximum or high intensity light signal reaches the associated detector whereas, for a perpendicular orientation of the grating lines relative to the ridge lines, that associated detector receives a minimum light signal.

The illustrative embodiment disclosed in the detailed description to follow is categorized broadly as an off-axis system. The aforementioned designation "on-axis" simply implies that the rotational axis of the optical grating is coincident with the axis of the light beam used in the apparatus and, likewise, the designation "off-axis" indicates that the axis of the light beam is displaced laterally from the rotational axis of the optical grating. Certain advantages accrue from the off-axis system and, for this reason, it is presently illustrated as constituting the preferred embodiment. In any case, it should be understood that, for ridge lines of any particular orientation, the conditions of minimum and maximum light intensity occur as described herein, irrespective of the location of the related ridge lines in the total area of the fingerprint under inspection. Because a particular detector is uniquely associated with each sampled area of the fingerprint, the time of occurrence of the minimum or maximum signal at the respective detectors during the course of a revolution of the grating is uniquely related to an individual and particular fingerprint. Thus, a fingerprint can be encoded according to the invention by noting the time lapse subsequent to any arbitrary time reference or spatial orientation of the optical grating at which an extremum value of light intensity occurs at the respective detectors and coverting these time intervals to equivalent analog or digital signals representative of the fingerprint as in the aforementioned McMahon patent.

Figure 2:
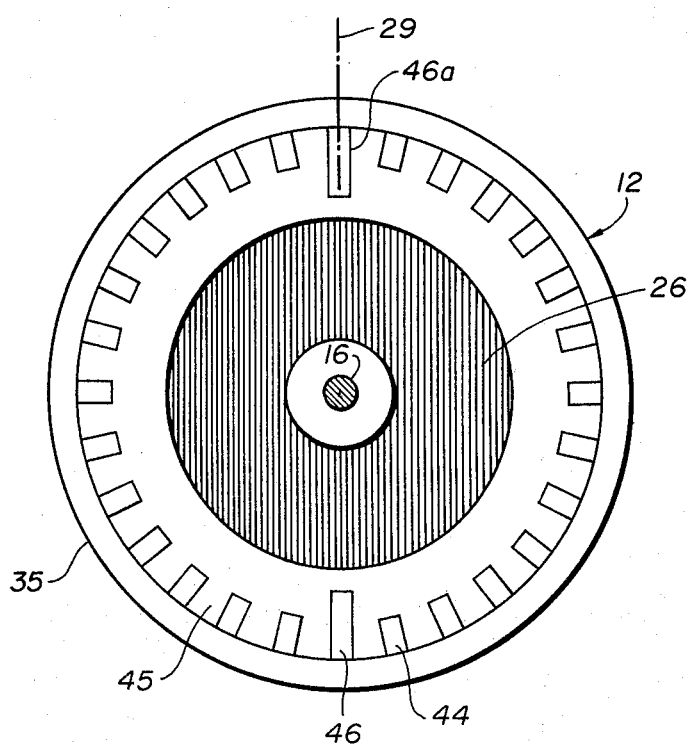
FIGS. 2 and 3 are respective elevation and side views of a rotatable grating element for use in the apparatus of FIG. 1.

Referring now specifically to FIGS. 1 and 2, light emitted by the incoherent light source 10 is collected by lens 11 and is converged onto region 13 of the optical grating element 12 which has at least alternate parallel light transmissive and reflective stripes (as generally shown in FIG. 2) and which is rotatable about its central axis 16 by motor 15. The light propagated through the transmissive portions of grating 26 of grating element 12 forms a light beam 23 directed through the lower half of lens 17 and onto retroreflecting prism 18, from which the incident beam is reflected as beam 24 and is directed through the upper half of lens 17 onto the portion of the grating 26 originally irradiated by the light from lens 11. Lens 17 is spaced from the optical grating 26 by a distance equal to the focal length of the lens 17. Consequently, an image of the grating 26 is produced, superposed on the grating 26 itself, as is further described in the aforementioned McMahon patent. In the case of the apparatus of FIG. 1, the image is erect so that the illuminated and dark image stripes coincide with the transmissive and reflecting grating stripes, respectively. Thus, in the absence of a fingerprint placed in contact with the retroreflecting prism 18, the light of the superposed image simply propagates back through the grating region 13 toward the light source 10, leaving essentially no light available to be reflected and collected by imaging lens 22 for transmission to the planar two dimensional photodetector array 19 positioned in a plane designated as image plane 20.

In the presence, for example, of a finger 21 placed on the top surface of the retroreflecting prism 18, light is diffracted by the ridge lines of the finger 21 similar to the diffraction produced by a finger print residing on a transparency, as is well known to those skilled in the art, whereupon the diffracted part of the light in beam 24 impinges on the reflective stripes of the grating 26 thereupon to be reflected, by virtue of the canted orientation of the rotatable grating 26 relative to the light beam 24, through imaging lens 22 to the rectangular photodetector array 19. The disposition of the detectors of array 19 for sampling discrete areas of the fingerprint is the same as explained within the aforementioned McMahon patent. The dashed line 25 depicts the apparent optical position of the finger 21, taking into account the well known refractive index properties of the prism 18. As indicated, the apparent position is sloped relative to the actual finger orientation and, therefore, the plane of the detector array 20 is similarly sloped in order for the entire fingerprint image to be in focus at the detector array 19. Transparency recording 36 (FIG. 4) may be positioned proximate the light entrance and exit surface 25 of prism 18 adjacent lens 17.

Figure 3:
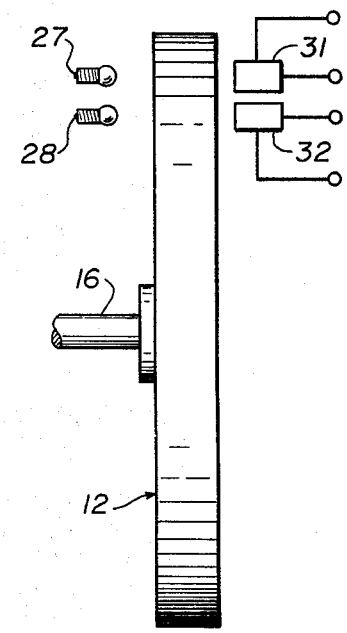

The rotatable grating element 12 may be of the general type illustrated in FIGS. 2 and 3 and also in FIG. 1 of the aforementioned McMahon patent. In the off-axis version of the present invention, the grating element 12 is supported for rotation about shaft 16 and includes the ring shaped grating 26 whose detailed character will later be described in connection with FIGS. 5 and 6.

In addition to grating 26, the rotatable grating element 12 includes at its periphery two series of optical pickoff elements for generating respective timing and reset pulse wave forms. These wave forms aid in the measurement of the time of occurrence of the successive maximum signal events at each of the detectors of photodetector array 19 for permitting encoding of the fingerprint pattern under investigation, as is further described in the aforementioned McMahon patent.

Referring again to FIGS. 2 and 3, the rotatable grating element 12 is equipped with an optical reference pickoff system utilizing light source 27 cooperating to supply one set of pulse reference output signals at the terminals of photocell 31. Similarly, light source 28 cyclically activates photocell 32 to supply corresponding output pulses. These two types of reference signals are utilized in the processing arrangements yet to be discussed in regard to FIG. 7. In FIG. 2, the periphery of the grating element 12 contains alternating transparent and opaque sections such as 44 and 45, respectively, which sections function in combination with the light source 27 and photocell 31 for generating reference timing pulses to be applied to the counter 65 of the processing system on FIG. 7. Radially lengthened transparent sections 46, 46a on diametrically opposite sides of the grating element 12 function in conjunction with an additional light source 28 and light detector 32 for providing counter reset pulses to the apparatus of FIG. 7 for indicating crossings of the vertical reference line 29 by grating element 12. While optical pick-offs are illustrated in the drawings, known inductive, capacitive, or other pick-offs may be substituted.

Figure 7:
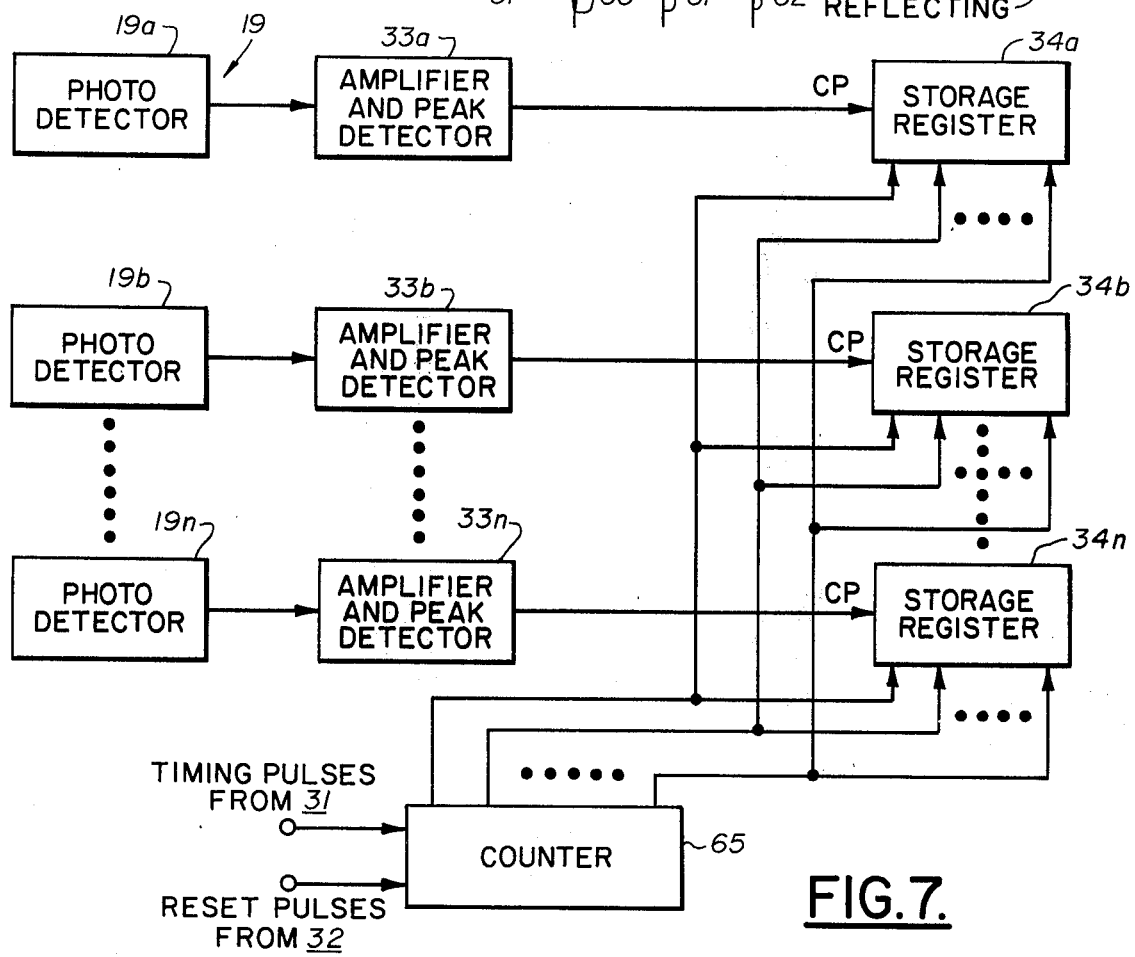
FIG. 7 is a block diagram of an electrical data processing system for use with the recognition apparatus of FIGS. 1 and 4.

Referring now particularly to FIGS. 1 and 7, it will be seen that as the grating element 12 rotates, any one photodetector of the photodetector array 19 may cyclically receive pulse signals corresponding to the features of a particular area of a fingerprint or transparency 36. For example, as in FIG. 1 of the aforementioned McMahon patent, a given sampled area of the print will produce a pulse of light in a particular and corresponding one of the detectors of array 19 at a time with respect to the reference pulse produced in reference pick-off photocell 32 characterizing the angle of the fingerprint ridges in the particular sampled area. This structure and operation will be fully understood from the foregoing; it may independently be understood by reference to the aforementioned McMahon patent. As the grating element 12 is rotated, successive impulses corresponding to each of the detectors 19a through 19n of the array 19 are respectively coupled, when present, from the detectors to corresponding amplifier and peak detector circuits 33a through 33n (FIG. 7).

Upon the crossing of the vertical reference line 29 of FIG. 2, counter 65 of FIG. 7 is reset to zero and a sequence of synchronized timing pulses, representing the grating element 12 orientation, is generated and is coupled from photodetector 32 to the counter 65. The stages of the counter, in turn, are coupled to the respective stages of an array of discrete storage registers 34a through 34n, each associated with one of the light detectors of the image plane detector array 19, and each having display capability. The number of pulses in the counter 65 at any one instant is representative of the angular position of the rotatable grating element 12 relative to the vertical 29. Thus, in the case, for instance, where one clock pulse represents 1° of rotation of grating element 12, counter 65 will have a count of 45° upon the grating element 12 reaching the position 45° counterclockwise from the vertical 29 in FIG. 2. If an electrical signal appears at the output of a peak detector at that instant of time, a corresponding conventional multi-bit storage register is enabled. Each one of the array of storage registers 34a through 34n includes a sufficient number of conventional latching circuits so as to represent the orientation of grating element 12 to the desired degree of accuracy. These latching circuits operate to accept input data only when a gating clock input signal is applied to the clock input terminal of each stage of the register. Thus, a digital signal representative of a particular count will be stored in the responding shift register representing the angular orientation of the ridge lines in a particular sampled area. Likewise, upon further rotation, the grating element 12 will transmit light corresponding to the ridge lines at a new sampled area and, at that instant, another photodetector will produce an electrical output signal which is applied through an associated peak detector to provide a clock pulse to the associated storage register so that a digital signal corresponding to a new instantaneous count is stored in that register. The same action occurs at each successive angle for which there is a detector in the image plane 20. As a consequence of the line symmetry of the rotatable grating element 12 and the parallel digital processing, it will be recognized that the digital representation of all the ridge angles of sample areas is generated in one-half revolution of element 12.

The present invention and that of the aforementioned McMahon patent are desirable systems in part because they do not require the use of expensive elements needed in coherent systems where, for example, an expensive coherent light source must be employed. A simple tungsten lamp may be used as light source 10 for illuminating the grating 26. In the aforementioned McMahon patent, the optical grating would consist of an array of parallel alternate light reflecting and transmitting stripes each about 0.02 inches wide. Thus, about half of the incident light is transmitted toward the prism 18, lens 17 and prism 18 serving to re-image most of that light back onto the grating 26. This re-imaged light, in the absence of a diffracting fingerprint, is simply transmitted back toward source 10. In effect, a kind of Schlieren system results which, regardless of the orientation of the grating 12, prevents any light from traveling from prism 18 toward detector array 19.

Now, should a finger surface be placed against prism 18 as shown in FIG. 1, light is consequently diffracted by the ridges of the finger through a small angle out of the forward direction so that it hits the reflective part of the ruling and is transmitted toward detector array 19. For example, if one small area of the fingerprint consists of vertical ridges or lines, light will be diffracted in a horizontal plane away from the forward direction; the diffracted light for all wave lengths will fall in this same horizontal plane. Consequently, there will always be some such light that will be reflected by the grating 26 toward detector array 19 unless the grating lines are horizontal. In general, some diffracted light from any given region of the fingerprint pattern will be reflected by grating 12 toward detector array 19 unless the lines of the grating are exactly perpendicular to the ridge lines for the sampled region. All diffracted light which is reflected from grating 12 is focused to form an image of the fingerprint pattern coincident with the plane 20 of the detector array 19. Consequently, the direction of the fingerprint lines at any given detection position of the fingerprint pattern can be determined by rotating the grating 26.

In the system of the prior McMahon patent, the lens 17 used to re-image the grating image upon the grating 26 itself is a critical element, an expensive achromatic doublet lens of long focal length being required to achieve perfect operation. When relatively short focal length lenses or lenses uncorrected for aberration are used, there exists an undesired background of light reaching detector array 19 which fluctuates in amplitude synchronously as the grating is rotated. The undesired light is found to be undiffracted light that is undesirably reflected by the reflecting surfaces of the grating; the major source of this undesired light is found to be due to lens aberrations which prevent light passed by grating 26 from being perfectly re-imaged back on the transparent portions of the grating. That is, some light which should be transmitted near the edge of the reflecting stripe is in fact incorrectly imaged so that it is reflected into the detector array 19. Calculations indicate that such re-imaging errors of the order of a few microns can cause a significant amount of undiffracted light to be reflected by the grating 26. This undesired light then fluctuates in amplitude in synchronism with the rotation of grating 26, producing a spurious light signal similar in characteristics to the desired diffracted light signal from the fingerprint pattern.

Figure 8:
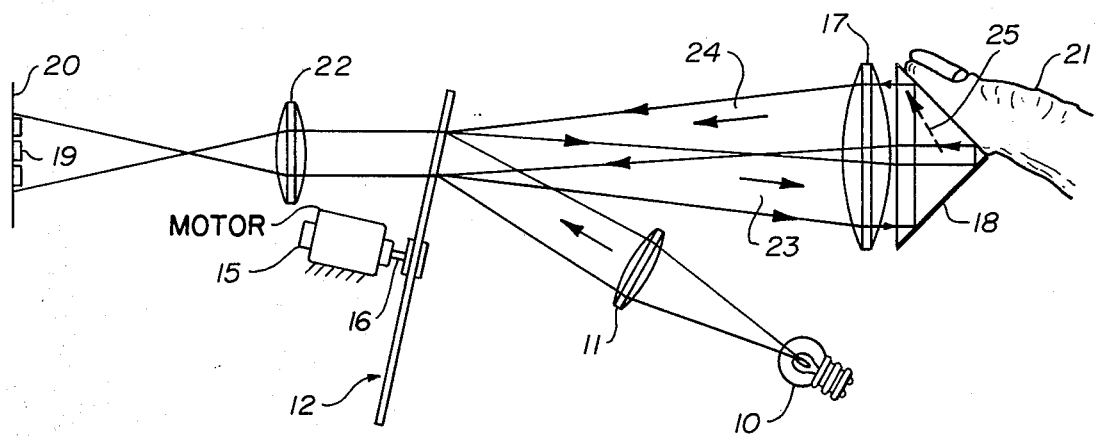
FIG. 8 is a block diagram of an alternative form of the system of FIG. 1 in which the novel rotatable grating element of FIGS. 2 and 3 may also be used.

The same problem is observed to be present in an embodiment of FIG. 1 in which the locations of light source 10 and of the photodetector array 19 are simply interchanged, as in FIG. 8, and the solution of the present invention is again applicable. The same elements are present in the re-arranged configuration of FIG. 8 as in FIG. 1, and they bear corresponding reference numerals. It will be seen that the system illustrated in FIG. 8 is generally analogous to that of FIG. 2 of the aforementioned McMahon patent. If the grating 26 employed in the rotatable grating element 12 is similar to that of the aforementioned McMahon patent, it again employs a grating consisting of an array of parallel alternate reflecting and transmitting stripes. In this situation, about one-half of the energy from light source 10 is reflected by the grating back toward prism 18, the retro-reflector prism 18 and the adjacent lens 17 serving to re-image light from grating 26 back upon the grating itself. This re-imaged light again forms an uninverted, unmagnified image which now falls on the reflective stripes of the grating 26 and is consequently reflected back into light source 10 in the absence of a fingerprint pattern.

If a fingerprint pattern is present at prism 18, the light diffracted by the ridges of the pattern is directed through a small angle out of the forward reflection direction and may not fall on reflecting parts of grating 26. Thus, some diffracted light energy passes through the transparent stripes of the grating, unless the lines of the grating are actually oriented perpendicular to the fingerprint ridge lines of the sampled region. All diffracted light which passes in this manner through the grating is focused by lens 22 to form an image of the fingerprint transparency in the plane 20 of the array 19 of light detectors. It is seen that this mode of operation is similar to that of the system of FIG. 1, light transmitted by the grating 26 being used to form the image rather than light reflected by the grating as in FIG. 1.

Aberrations present in lens 17 again produce a problem, causing generation of undesired signals in the photodetector array 19. In this instance, the major portion of the undesired light is due to aberrations in lens 17 which prevent light reflected from the reflecting portions of grating 26 from being perfectly imaged back on to those same reflecting portions. That is, some light which should be reflected near the edges of the reflecting stripes is in fact re-imaged, passing through the grating. This undesired light signal again fluctuates in amplitude in synchronization with the rotation of the grating element 12, producing undesired pulses in the outputs of the detectors of array 19 similar in characteristics to the desired signals.

Figure 5:
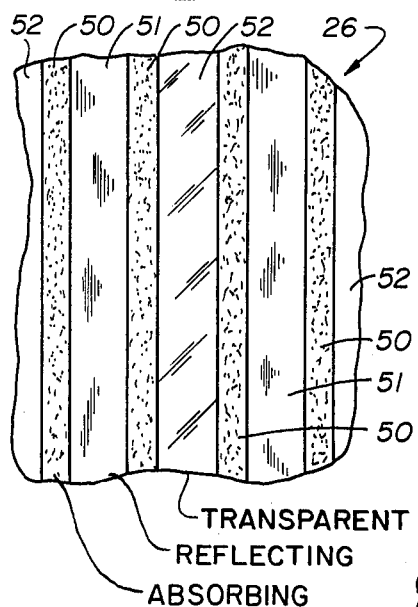
FIGS. 5 and 6 are elevation and cross section views, respectively, of a novel optical grating for use in the apparatus of FIGS. 1 through 3.
Figure 4:
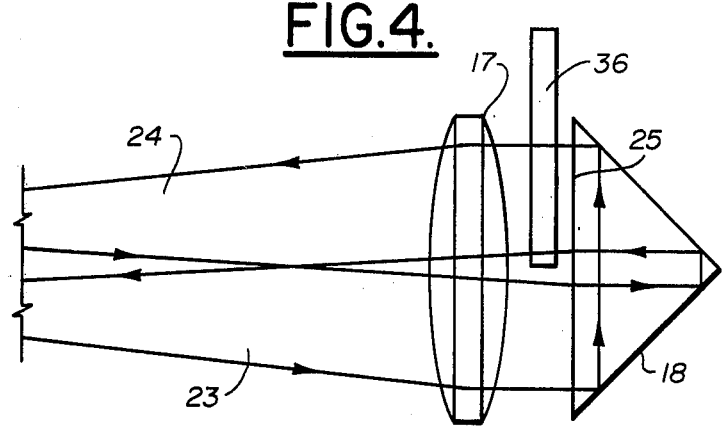
FIG. 4 is an elevation view illustrating an alternative arrangement of part of FIG. 1.
Figure 6:
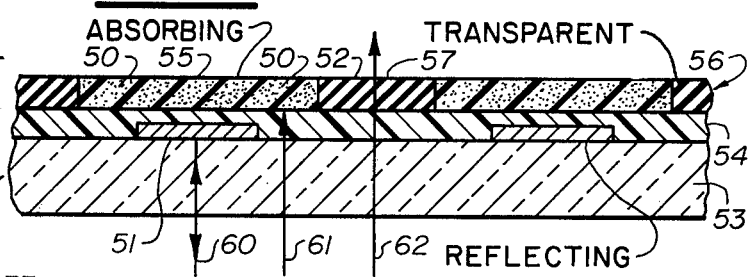

According to the present invention, a rotatable grating element of improved nature is employed in place of the grating of the prior McMahon patent which was composed of a simple regular pattern of alternate transparent and reflecting stripes. The novel composite grating eliminates the undesired light generated by lens aberrations and off axis geometry and is illustrated in FIGS. 5 and 6, FIG. 5 being drawn at one scale and FIG. 6 at a considerably larger scale for the sake of clarity. As is seen in FIG. 5, the novel grating 26 appears from the illuminated side to have parallel alternate reflecting and transmitting stripes 51 and 52 located in a regular array and of substantially the same widths. Interposed between each transmitting and reflecting stripe is a light absorbing stripe 50 whose width is substantially one half of the width of each of the other stripes.

The novel grating structure 26 may be manufactured in any of several ways, each of which employ substantially conventional steps. One way of making the grating will be discussed in connection with FIGS. 5 and 6. The grating 26 is built up on a glass substrate 53 having a contour suitable for direct installation in the grating element 12, as shown in FIG. 2. After suitable cleaning, parallel stripes 51 of a reflecting metal are generated on one surface of substrate 53. The metal stripes are substantially one half the widths of the transparent stripes between them. These stripes 51 may be formed by using any suitable, well-established process, such as one of the standard photoetching processes. Alternatively, a surface of substrate 53 may be completely covered with a thin layer of metal, such as a layer of chromium on layers of chromium and aluminum. After generating such metal layers, as by evaporation in a vacuum, material may be removed by use of photoetching techniques or by an energetic laser or electron beam, removing the material so as to leave parallel reflecting stripes 51 of metal separated by transparent stripes 52 where the metal has been removed.

The resulting structure is next used directly to develop an additional portion of the final grating. For example, a photographic film 56 may be exposed by contact printing directly through substrate 53 with its metal stripes 51. When the film is developed, it has opaque stripes 55 which are twice as wide as the metal stripes 51. The substrate and metal stripes are coated with a suitable adhesive at 54, such as a commercially available epoxy cement which remains transparent after it hardens. The exposed film is translated relative to the reflecting stripes 51 and is placed against the cement, after which the cement hardens.

The resulting structure as seen in FIGS. 5 and 6 has reflecting metal stripes 51 on a surface of the substrate 53. The cement layer, exaggerated in thickness, is identified at 54. The photographic film 56 is seen to be made up of transparent stripes 57 and opaque or light absorbing stripes 55. The absorbing stripes 55 are now seen centered behind the reflecting stripes 51 in such a way that on each side of the reflecting stripe 51 there appears the reduced width absorbing stripes 50. In operation, a light ray 60 which strikes the substrate side of reflecting layer 51 is seen to be reflected. A light ray 61 impinging upon the reduced width absorbing stripe 50 is simply absorbed. It is understood that the absorption process may be one in which the optical energy is truly absorbed or is scattered widely with respect to the optical axis of the system. In general, both mechanisms are useful and may be simultaneously present. A light ray 62 passes through the structure via transparent stripe 57.

When the invention is operated with the novel grating 26 in use, it is found that undesired leakage light is greatly reduced. The composite grating of FIGS. 5 and 6 thus permits achievement of an incoherent light filtering system in which undesired light signals of the aforementioned type are greatly reduced in amplitude. The use of the composite grating structure not only reduces interference due to such leakage light, but is also valuable because it permits the use of less expensive and shorter focus, less corrected lenses. In addition, there has been discussed in the foregoing the advantage of using off-axis arrangements such as those shown in FIGS. 1 and 2. It is evident that these systems would require expensive lenses permitting considerable depth of focus because of the tilt of the grating 26 with respect to the plane of the lens 17. Thus, even a perfectly corrected lens will not function correctly in such off-axis systems. However, the composite grating of the present invention eliminates this problem, sharp focusing no longer being a requirement.

Apparatus embodying the inventive concept may be used in the following manner. Initially, a known fingerprint may be digitally encoded by placing it at the data input of the processor. Encoding is then accomplished by generating a sequence of synchronized timing pulses representative of the grating orientation relative to a reference orientation and applying the pulses to a digital counter. The counter is coupled to a plurality of multistage storage registers for parallel digital signal processing. When the signal amplitude of each photodetector abruptly changes, a gate pulse is applied to the stages of the associated storage register, causing the instantaneous contents of the counter to be transferred to that register. As a result of this action, each storage register ultimately contains a unique set of binary signals representative of the ridge line orientation of discrete sampled areas of the known fingerprint. The same procedure is followed for each fingerprint desired to be encoded and stored and the encoded signals representative of the various fingerprints are stored in any convenient manner suitable for rapid access and subsequent correlation with encoded signals obtained in the course of inspecting fingerprints at some later time for the purpose of identification. Identification is made when a fingerprint presented for inspection produces encoded signals identical or at least substantially identical to one of the sets of stored encoded signals, for which condition autocorrelation of the input and stored signals results.

While the invention has been described in its preferred embodiments, it is to be understood that the words which have been used are words of description rather than of limitation and that changes may be made within the purview of the appended claims without departing from the true scope and spirit of the invention in its broadest aspects.

I claim:
1. In pattern recognition apparatus:
rotatable support means having a regular array of alternating parallel elongate spaced light transmitting and reflecting elements,
light source means for illuminating said regular array,
retroreflective means including focusing means for forming an image of said regular array in substantial but imperfect alignment with said regular array,
elongate light absorbing elements disposed between each of said alternate parallel elongate light transmitting and reflecting elements for substantially eliminating light misdirected because of said imperfect alignment,
said retroreflective means including surface means for supporting an input pattern to be recognized in the light received by said retroreflective means from said regular array of elongate elements,
said input pattern being characterized by light transmissive or reflective lines of varying orientation over the area of said input pattern and having the effect, when present at said input pattern supporting surface means and when said rotatable means is rotating, of variably diffracting light from said image of said regular array onto said regular array, and
signal processing means responsive to the position of said rotatable support means and to said variably diffracted light directed by said regular array for determining the angular orientation of said rotatable support means with respect to a reference position thereof at the instants of extremum values of light intensity of said variably diffracted light.
2. Apparatus as described in claim 1 further including:
motive means for rotating said rotatable support means,
said signal processor means including sensor means responsive to indicia disposed on said rotatable support means for generating signals representative of the angular orientation of said rotatable means with respect to a reference position thereof.
3. Apparatus as described in claim 2 wherein said signal processing means further includes a light detector array disposed for receiving said variably diffracted light directed thereto by said regular array.
4. Apparatus as described in claim 3 wherein:
said light source is disposed on a first side of the plane of said rotatable support means,
said retroreflective means is disposed on a second side of said plane, and
said variably diffracted light is reflected by said regular array into said light detector array,
said light detector array being disposed on the second side of said plane.
5. Apparatus as described in claim 3 wherein:
said light source is disposed on a first side of the plane of said rotatable support means,
said retroreflective means is disposed on said first side, and
said variably diffracted light is transmitted by said regular array into said light detector array,
said light detector array being disposed on a second side of said array.

* * * * *